US009931383B2

(12) United States Patent
Sanders

(10) Patent No.: US 9,931,383 B2
(45) Date of Patent: *Apr. 3, 2018

(54) TREATMENT OF MAMMALIAN PHYSIOLOGICAL REACTION OF IGE ANTIBODIES PRESENT IN SAID MAMMAL UPON CONTACT WITH THE CORRESPONDING ANTIGEN

(71) Applicant: Ira Sanders, North Bergen, NJ (US)

(72) Inventor: Ira Sanders, North Bergen, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/083,540

(22) Filed: Mar. 29, 2016

(65) Prior Publication Data

US 2016/0206711 A1    Jul. 21, 2016

Related U.S. Application Data

(63) Continuation of application No. 14/223,056, filed on Mar. 24, 2014, now Pat. No. 9,314,513, which is a continuation of application No. 12/976,459, filed on Dec. 22, 2010, now Pat. No. 8,715,620, which is a continuation of application No. 10/535,504, filed as application No. PCT/US03/37286 on Nov. 20, 2003, now Pat. No. 7,879,340.

(60) Provisional application No. 60/427,749, filed on Nov. 21, 2002.

(51) Int. Cl.
| | |
|---|---|
| *A61K 39/08* | (2006.01) |
| *A61K 49/00* | (2006.01) |
| *A61K 39/38* | (2006.01) |
| *A61K 38/48* | (2006.01) |
| *A61K 38/16* | (2006.01) |
| *C12N 15/74* | (2006.01) |
| *A61K 9/00* | (2006.01) |
| *A61K 48/00* | (2006.01) |
| *A61K 39/00* | (2006.01) |
| *A61K 38/00* | (2006.01) |

(52) U.S. Cl.
CPC .......... *A61K 38/4893* (2013.01); *A61K 9/007* (2013.01); *A61K 9/0019* (2013.01); *A61K 9/0031* (2013.01); *A61K 9/0043* (2013.01); *A61K 9/0046* (2013.01); *A61K 9/0073* (2013.01); *A61K 38/164* (2013.01); *C12N 15/74* (2013.01); *A61K 38/00* (2013.01); *A61K 48/00* (2013.01); *A61K 2039/543* (2013.01); *C12Y 304/24069* (2013.01)

(58) Field of Classification Search
CPC ........ A61K 39/00; A61K 39/02; A61K 39/08; A61K 39/35; A61K 2039/00; A61K 2039/545; A61K 2039/55544
USPC ..... 424/9.1, 9.2, 130.1, 139.1, 171.1, 184.1, 424/234.1, 236.1, 239.1, 247.1, 278.1
See application file for complete search history.

(56) References Cited

U.S. PATENT DOCUMENTS

| | | | |
|---|---|---|---|
| 5,510,339 A | 4/1996 | Gleich et al. | |
| 5,670,484 A | 9/1997 | Binder | |
| 6,063,768 A | 5/2000 | First | |
| 6,429,189 B1 | 8/2002 | Borodic | |
| 6,822,076 B2 | 11/2004 | Bigalke et al. | |
| 7,537,773 B1 | 5/2009 | Borodic | |
| 7,608,275 B2 | 10/2009 | Deem et al. | |
| 7,655,243 B2 | 2/2010 | Deem et al. | |
| 7,879,340 B2 * | 2/2011 | Sanders ............... | A61K 38/164 424/130.1 |
| 8,088,361 B2 * | 1/2012 | Sanders ............... | A61K 38/164 424/130.1 |
| 2002/0082197 A1 | 6/2002 | Aoki et al. | |
| 2003/0157134 A1 | 8/2003 | Aoki et al. | |
| 2004/0247606 A1 | 12/2004 | Borodic et al. | |
| 2006/0008462 A1 | 1/2006 | Sanders | |
| 2011/0086072 A1 | 4/2011 | Sanders | |
| 2011/0091504 A1 | 4/2011 | Sanders | |
| 2011/0091505 A1 | 4/2011 | Sanders | |
| 2011/0150975 A1 | 6/2011 | Sanders | |
| 2012/0071395 A1 | 3/2012 | Sanders | |
| 2014/0286930 A1 | 9/2014 | Sanders | |

FOREIGN PATENT DOCUMENTS

| | | |
|---|---|---|
| CA | 2507115 A1 | 6/2004 |
| CA | 2854831 A1 | 6/2004 |
| EP | 1565210 B1 | 1/2012 |
| WO | WO-9528171 A1 | 10/1995 |
| WO | WO-0015245 A2 | 3/2000 |
| WO | WO-0200172 A2 | 1/2002 |
| WO | WO-2004048519 A2 | 6/2004 |

OTHER PUBLICATIONS

Fan, Clinical types of childhood asthma and nonatopic asthma. World J. Pediatrics, 2(2):85-89, 2006.
Hoffman, Hans Jurgen, et al., SNARE Proteins Are Critical for Regulated Exocytosis of ECP from Human Eosinophils, Biochemical and Biophysical Research Communications, 282:194-199, 2001.
Hurwitz et al., Nonallergic asthma: Differential diagnosis and treatment Cal. Med., 83(2):61-67, 1995.
Logan, UR., et al., A Critical Role for Vesicle-Associated Membrane Protein-7 in Exocytosis for Human Eosinophils Neutrophils, Allergy, 61:777-784, 2006.
Mazzone, Stuart B., et al., Evidence for Differential Reflex Regulation of Cholinergic and Noncholinergic Parasympathetic Nerves Innervating the Airways. American Journal of Respiratory and Critical Care Medicine, 165:1076-1083, 2002.

(Continued)

*Primary Examiner* — Rodney P Swartz
(74) *Attorney, Agent, or Firm* — Ted A. Chan

(57) ABSTRACT

A method is disclosed for blocking or reducing physiological reaction in a mammal to the interaction of IgE antibodies present in said mammal upon contact with the corresponding antigen, by the administration to said mammal of a therapeutically effective amount of a neurotoxin (CnT) derived from *Clostridia* sp.

17 Claims, No Drawings

(56) References Cited

OTHER PUBLICATIONS

PCT/US2003/037286 International Preliminary Examination Report dated Mar. 25, 2005.
PCT/US2003/037286 International Search Report dated May 24, 2004.
Rohrbach, S., et al., Botulinum Toxin Type A Induces Apoptosis in Nasal Glands of Guinea Pigs, Annals of Otology, Rhinology and Laryngology. 101:1045-1050, 2001.
Rohrbach, S., et al., Minimally Invasive Application of Botulinum Toxin Type A in Nasal Hypersecretion, Journal for and its Related Specialties, 63(6):382-384, 2001.
Shaari et al., Rhinorrhea is decreased in dogs after nasal application of botulinum toxin. Otolaryngology Head and Neck Surgery, 112(4):566-571 (1995).
Unal, Murat, et al., "Effect of Botulinum Toxin Type A on Nasal Symptoms in Patients with Allergic Rhinitis: A Double-Blind, Placebo-Controlled Clinical Trial," Acta Otolaryngol, 123:1060-1063, 2003.
U.S. Appl. No. 10/535,504 Office Action dated Dec. 3, 2008.
U.S. Appl. No. 10/535,504 Office Action dated Feb. 18, 2010.
U.S. Appl. No. 10/535,504 Office Action dated Feb. 4, 2009.
U.S. Appl. No. 10/535,504 Office Action dated Sep. 12, 2007.
U.S. Appl. No. 12/976,459 Office Action dated Dec. 19, 2012.
U.S. Appl. No. 12/976,459 Office Action dated Jun. 8, 2011.
U.S. Appl. No. 12/976,459 Office Action dated Mar. 13, 2012.
U.S. Appl. No. 12/976,459 Office Action dated Sep. 13, 2012.
U.S. Appl. No. 12/976,459 Office Action dated Sep. 23, 2011.
U.S. Appl. No. 12/976,459 Office Action dated Sep. 24, 2013.
U.S. Appl. No. 13/304,092 Office Action dated Mar. 15, 2012.
U.S. Appl. No. 14/223,056 Office Action dated Jun. 26, 2014.
U.S. Appl. No. 14/223,056 Office Action dated Mar. 24, 2015.
Kim et al., The effect of botulinum toxin type A injection for intrinsic rhinitis. The Journal of Laryngology and Otology, 112:248-251, 1998.
Borodic et al., Botulinum toxin therapy for pain and inflammatory disorders: mechanisms and therapeutic effects. Expert Opinion on Investigational Drugs, 10(8):1531-1544, 2001.
"Clostridium baratti." Database NCBI Taxonomy Browser [Online], National Center for Biotechnology Information, 3 pages, retrieved from the internet on Jan. 19, 2017 at: http://www.ncbi.nlm.nih.gov/taxonomy/tax.html.
Dines et al., Mast cell interactions with the nervous system: relationship to mechanisms of disease. Journal of Neuropathology and Experimental Neurology, 56(6):627-640, 1997. Abstract only.
European Patent Application No. 03786972.4 Communication dated Feb. 25, 2009.
European Patent Application No. 03786972.4 Communication dated Mar. 18, 2008.
European Patent Application No. 03786972.4 Supplementary European Search Report dated Nov. 23, 2007.
Gergen and Turkeltaub, The association of individual allergen reactivity with respiratory disease in a national sample: data from the second National Health and Nutrition Examination Survey, 1976-80 (NHANES II). J. Allergy Clin. Immunol., 90(4 Pt. 1):579-588, 1992. Abstract only.
Ira Sanders Declaration dated Jun. 1, 2008, 4 pages.
Kulka et al., Neuropeptides activate human mast cell degranulation and chemokine production. Immunology, 123:398-410, 2007.
Monteforte et al., Morphological changes in frog mast cells induced by nerve stimulation in vivo. Neuroscience Letters, 315:77-80, 2001.
Ozcan et al., The effect of intranasal injection of botulinum toxin A on the symptoms of vasomotor rhinitis. ScienceDirect, American Journal of Otolaryngology-Head and Neck Medicine and Surgery, 27:314-318, 2006.
Pearce et al., How much asthma is really attributable to atopy? Thorax, 54:268-272, 1999.
Shibasaki et al., Botulinum toxin abolishes sweating via impaired sweat gland responsiveness to exogenous acetylcholine. British Journal of Dermatology, 5 pages, 2009.
Shukla et al., Regulated exocytosis in immune function: are SNARE-proteins involved? Respiratory Medicine, 95:773-780, 2001.
Yang et al., A comparison of the effects of botulinum toxin A and steroid injection on nasal allergy. Otolaryngology-Head and Neck Surgery, 139:367-371, 2008.

\* cited by examiner

TREATMENT OF MAMMALIAN PHYSIOLOGICAL REACTION OF IGE ANTIBODIES PRESENT IN SAID MAMMAL UPON CONTACT WITH THE CORRESPONDING ANTIGEN

CROSS-REFERENCE

This application is a continuation of U.S. patent application Ser. No. 14/223,056, filed Mar. 24, 2014, now U.S. Pat. No. 9,314,513, which is a continuation of U.S. patent application Ser. No. 12/976,459, filed Dec. 22, 2010, now U.S. Pat. No. 8,715,620, which is a continuation of U.S. patent application Ser. No. 10/535,504, filed May 18, 2005, now U.S. Pat. No. 7,879,340, which is a national stage entry of PCT Appl. No. PCT/US03/37286, filed on Nov. 20, 2003, claims the benefit of priority U.S. Provisional Application No. 60/427,749, filed Nov. 21, 2002, each of which incorporated herein by reference in their entirety.

FIELD OF THE INVENTION

A method is disclosed for blocking or reducing physiological reaction in a mammal to the interaction of IgE antibodies present in said mammal upon contact with the corresponding antigen, by the administration to said mammal of a therapeutically effective amount of a neurotoxin (CnT) derived from *Clostridia* sp.

BACKGROUND OF THE INVENTION

Throughout this application various publications are referred to within parentheses or by footnote. The contents of these publications are hereby incorporated by reference in their entirety.
Introduction The physiological reaction in a mammal to the interaction of IgE antibodies present in said mammal upon contact with the corresponding antigen is generally referred to as allergy. It is believed that the allergic response evolved to combat infections with parasites. As parasitic infections are rare in industrialized countries this mechanism becomes pathologic in certain susceptible (atopic) individuals. Characteristic of allergies is that the antigen, also called the allergen, is normally innocuous, and the body's reaction is inappropriate.

Allergic reactions can involve all body tissues but are most prominent in the boundaries with the external environment: the airway, eye, gastrointestinal tract and skin. The conditions are known as allergic rhinitis in the nose (hay fever), allergic asthma in the lungs, food allergies in the GI tract and allergic hypersensitivity (hives) or dermatitis in the skin. Anaphylaxis refers to the systemic reaction that occurs when an allergen is introduced directly into the circulation, such as occurs with injection of drugs and insect stings. A massive early phase reaction occurs throughout the body. Symptoms include diffuse airway swelling and hypotension which can be life threatening.

Each year more than 50 million Americans suffer from allergic diseases, costing the health care system $18 billion annually (American Academy of Allergy, Asthma and Immunology (AAAAI). The Allergy Report: Science Based Findings on the Diagnosis & Treatment of Allergic Disorders, 1996-2001)

Alarmingly, the prevalence and severity of allergic disorders has rapidly increased in the United States over the past twenty years, so there is a need for new therapies for these conditions.

In 1998, an estimated 15 million Americans, or 6.4 percent of the population, had asthma, with 5 million being children. Children account for 4.8 million of Americans with asthma. Each year, 1.8 million emergency room visits are for asthma, nearly 500,000 Americans are hospitalized and more than 5,000 die from the disease. Although asthma deaths are infrequent, they have increased significantly during the last two decades. From 1975-1979, the death rate was 8.2 per 100,000 people. That rate jumped in 1993-1995 to 17.9 per 100,000. Asthma cost the U.S. economy an estimated $10.7 billion in 1994, including a direct health care cost of $6.1 billion and indirect costs, such as lost workdays, of $4.6 billion.

Approximately 16.7 million office visits to health care providers each year are attributed to allergic rhinitis alone (CDC. Fast Stats A-Z, Vital and Health Statistics, Series 10, no. 13. 1999

A related condition, chronic sinusitis, is the most commonly reported chronic disease, affecting 12.6 percent of people (approximately 38 million) in the United States in 1996. Another related condition, serous otitis media, is the most common condition in children requiring an office visit to a health care provider.

Atopic dermatitis is one of the most common skin diseases, particularly in infants and children. The estimated prevalence in the United States is 9 percent Rudikoff D and Lebwohl M. "Atopic dermatitis." Lancet 351(9117): 1715-21. 1998.

Experts estimate that food allergy occurs in 8 percent of children 6 years of age or under, and in 1 to 2 percent of adults Sampson H A. In Allergy, Principles and Practice, $5^{th}$ Ed., E. Middleton et al, ed. Mosby, St. Louis, p. 1162. 1998.
Pathophysiology of Allergy Allergy is an ailment that affects millions of individuals worldwide. Attempts to desensitize an individual against a material that causes an allergic response (hereafter designated as an "allergen") by injection of measured dosages of the allergen heretofore has failed to achieve complete relief of allergy symptoms reproducibly in all allergic individuals. An allergic response is a term of art and has a well-defined meaning. Within the context of the present invention, an allergic or reagenic response includes, in particular, at least one of the features of 1.) production of an abnormally high level of IgE in an individual's serum, 2.) immunologic interaction between an allergen, an individual's IgE and leukocytes resulting in release of histamines, 3.) production of hives, rashes, wheal and flare and similar dermatological manifestation of hypersensitivity, and 4.) anaphylaxis.

An allergic response is a state of hypersensitivity in which an exaggerated immune response is induced by the exposure to a particular antigen or allergen. Hypersensitivity reactions can be classified as immediate or delayed. Immediate or type I hypersensitivity (or anaphylactic response) is an allergic reaction which develops very quickly, i.e., within seconds or minutes of exposure of the patient to the causative allergen, and it is mediated by IgE antibodies produced by B lymphocytes. In non-allergic patients, there is no IgE antibody of clinical relevance. However, in a person suffering with allergic diseases, IgE antibody mediates immediate hypersensitivity by sensitizing mast cells which are abundant in the skin, membranes of the eye, nose and mouth, and in the respiratory tract and intestines.

IgE secreted from activated B cells can attach to Fc receptors located on the surface of mast cells and basophil granulocytes, which contain numerous cytoplasmic granules packed with chemical mediators e.g. histamine (J. Klein, "Immunology", Blackwell Sci. Pub., London, 1990; E.

Benjamini & S. Leskowitz, "Immunology", Wiley-Liss, N.Y. 1991). This receptor binds circulating IgE with very high affinity and retains it at the mast cell surface for extended periods of time. Activation is accomplished through the binding of an allergen simultaneously to more than one polyvalent molecule of Fc receptor-bound IgE. This "cross linking" of at least two surface-bound IgE molecules brings Fc receptor proteins into close association with one another in the plane of the mast cell plasma membrane. When the bound IgE is contacted by the appropriate allergen, the mast cell becomes activated. Kinases associated with these receptors become activated as a result of this proximity. They initiate the second messenger cascade, which results in the fusion of the granules with the cell surface membrane, leading to the exocytosis of the granule contents, such as histamine, cytokines, and leukotrienes into the surrounding tissue, and the concomitant induction of allergic symptoms. It is the activity of these substances which is responsible for the clinical symptoms typical of immediate hypersensitivity. These include contraction of smooth muscle in the airways or the intestine, the dilation of small blood vessels and the increase in their permeability to water and plasma proteins, the secretion of thick sticky mucus, and in the skin, swelling and the stimulation of nerve endings that results in itching.

Delayed type hypersensitivity (DTH) reactions are mediated by T-cells and macrophages and become evident only after 1 to 2 days and persist from several days to a few weeks. DTH is also referred to as cell-mediated hypersensitivity (i.e., T-cell mediated) and is part of a larger group of reactions called cell-mediated immunity.

Anaphylaxis, or anaphylactic shock, is an acute systemic (whole body) type of allergic reaction. It occurs when a person has become sensitized to a certain substance or allergen (that is, the immune system has been abnormally triggered to recognize that allergen as a threat to the body). On the second or subsequent exposure to the substance, an allergic reaction occurs. This reaction is sudden, severe, and involves the whole body. Anaphylaxis is life-threatening and can occur at any time.

Therapeutically, many agents are used to try to prevent the release of mediators from mast cells and basophils and/or to treat the downstream events by blocking or ameliorating the effects of the mediators on target tissues. Therapeutic agents commonly employed fall under the following main groups.

Antihistamines block and mop up the released histamine, i.e. the major mediator of the allergic response.

Agonists, e.g., Epinephrine, Salbutamol, overcome indirectly the downstream effects on vasculature and smooth muscle.

Chromoglycate is useful for primary prevention of mast cells/basophil degranulation. This prophylactic must be taken continuously. It does not prevent the cross-linking of IgE but it somehow interferes with subsequent events. Theophylline and other phosphodiesterase inhibitors again influence downstream biochemical events particularly associated with cyclic nucleotides. Steroids have multiple sites of activities against the allergic response. They are either administered locally and/or systematically.

None of the above treatments are ideal for the modulation of allergic responses because each has specific problems such as side effects including drowsiness, they also lack specificity in the immune system leading to global immunosuppression. Also many of these therapeutic agents need to be administered continuously. Therefore, new improved treatments are constantly being sought to control the allergic response prophylactically and/or therapeutically without the above-mentioned limitations.

Individuals who wish to become desensitized against an allergen often must submit himself/herself to injections of measured doses of the allergen, first administered at weekly or biweekly intervals, then gradually decreases to bimonthly or monthly intervals throughout the year. Such injections generally commence with a small dose of the allergen and then gradually increasing the dosage until a maximally-tolerated maintenance dose is achieved. The individual is then kept on a maintenance dose of the allergen for long periods of time or until the individual no longer exhibits an allergic reaction to the allergen.

Other treatment regimes have been devised to reduce or eliminate an allergic response.

Allergen injection therapy (allergen immunotherapy also known as subcutaneous immunotherapy (SCIT) is known to reduce the severity of allergic rhinitis. This treatment is theorized to involve the production of a different form of antibody, a protective antibody which is termed a "blocking antibody" (Cooke, R A et al., Serologic Evidence of Immunity with Coexisting Sensitization in a Type of Human Allergy, Exp. Med. 1935; 62:733). Chemical agents have been developed which inhibit the interactions between the IgE and its receptor (Cheng et al., U.S. Pat. No. 5,965,605 and Ra et al., U.S. Pat. No. 6,090,034). IgE antagonists have also been used to treat allergic disease (Presta et al., U.S. Pat. No. 5,965,709) and compounds that exhibit immunosuppressive activity and inhibits the release of histamine (Bycroft et al., U.S. Pat. No. 5,969,158). St. Remy et al., U.S. Pat. No. 4,740,371, discloses an immune complex of an allergen for treating allergies involving a combination of the specific allergen and the corresponding antibody to that allergen. The injection of the complex into a patient is said to reduce a patient's allergic reaction to that specific allergen. Others have suggested that certain human proteins can neutralize IgE by blocking it from interacting with the mast cells, but this has not been established clearly as a clinically effective therapy (Stanworth, et al., Allergy Treatment with a Peptide Vaccine, Lancet 1990; 336:1279-81). Patterson et al., U.S. Pat. No. 5,314,690 disclosed a method and preparations for reducing IgE antibodies to allergens in allergic subjects wherein substance P (a neuropeptide) and an allergen or fragments of allergens or haptens acting as allergens are administered together to the allergic subjects through a non-oral route.

Cholera Toxin and B Subunit as Adjuvants Cholera toxin (CT) and the closely related heat-labile toxin (LT) from *Escherichia coli* are known as exceptionally potent immunoadjuvants when co-administered with antigens by various mucosal routes (Elson et al., J. Immunol. 1984; 133:2892-2897; Hohngren et al., Vaccine 1973; 11: 1179-1184; Lycke et al, Eur. J. Immunol. 1992; 22:2277-2281. Both CT and LT are recognized as "AB" toxins in that they are composed of two distinct structural and functional components: a single toxic-active A subunit component and a non-toxic cell-binding B subunit. The latter is a homiopentamer component with strong binding affinity for GMI ganglioside receptors (Holingren et al., Nature 1981; 292:413-417). Such receptors are known to be present on most mammalian cells, e.g., on skin and other epithelial cells, on all known antigen-presenting cells including dendritic cells (DC) and Langerhan's cells (LC), as well as on B and T lymphocytes. Recently, Gleim et al., U.S. Pat. No. 5,980,898 disclosed a system for transcutaneous immunization that induces an immune response (e.g., humoral and/or cellular effectors) in an animal or human. The system provides a simple application to intact skin of both rodents and humans of a formulation comprised of antigen and an adjuvant that was whole cholera toxin.

Common to allergies is the involvement of the IgE class of antibody. Individuals are not born with allergies; rather they acquire them by exposure to allergens. The steps of the IgE allergic reaction are sensitization upon first exposure to the allergen, and then the allergic response to subsequent exposures. The allergic response consists of an immediate and delayed response referred to as the early and late phase responses respectively. In atopic individuals, those prone to allergies, the initial exposure to an antigen results in the production of IgE antibodies that specifically recognize that allergen. This process is called sensitization.

The early phase response (ERP) is the immediate reaction that occurs within minutes of exposure to an allergen. IgE are bound to the surface of a neuroimmune cell called the mast cell (in the circulation these cells are called basophils). Sufficient numbers of bound IgE antibodies that react with an allergen causes the mast cell to release its content of secretory vesicles, a process known as degranulation. The secretory vesicles contain histamine and other stored substances such as nerve growth factor (NGF). In addition the mast cell and T cells immediately begin manufacturing leukotrienes, cytokines, enzymes and substances that activate blood platelets and attract secondary cells such as eosinophils. Symptoms vary depending on the site, but common reactions are smooth muscle contraction, mucus secretion, vascular permeability, and sensory nerve stimulation.

The late phase response (LPR) develops over hours to days of exposure as eosinophils and other cells are attracted to the area. Eosinophils produce major basic protein, eosinophil cationic protein, leukotrienes and nerve growth factor. TH2 lymphocytes release cytokines that promote further IgE production and eosinophil chemo attraction, and increased numbers of mast cells.

Nerve Involvement in Allergy

The sensory nerve stimulation causes reflexes that are designed to aid in defending the tissue. These reflexes are often a larger problem then the local allergic response. Reflexes can range from large gross motor actions to regional afferent and efferent arcs or even local axon-axonal reflexes involving a single neuron.

Some reflexes recruit major motor actions that are well recognized. In the nose, sneezing is a reflex attempt to expel unwanted material and coughing is the equivalent response in the lungs.

Regional reflex arcs involve the sensing of the stimulus by the sensory neuron, the transfer of the message to the ganglia and the central nervous system and an efferent response via autonomic neurons. Reflex excitation by the autonomic nervous system directly causes mast cell to degranulate, thereby spreading the reaction. In addition these reflexes control a variety of other functions. In the nose these reflexes cause increased mucus production, increased cilia movement, nasal congestion and sneezing. In the lungs reflexes cause bronchospasm, increased mucosal congestion, production of airway secretions and coughing. In the GI tract reflexes cause dysmotility, mucosal congestion and secretions. In the skin the reflexes cause swelling and itching.

Finally there are local axon-axonal reflexes in sensory nociceptive nerve fibers. Allergic stimulation of a single neuron causes release of mediators from other axons of the same neuron. (Barnes P et al. 1991 Neuropeptides in the respiratory tract. Am Rev Resp Dis 144:1187-1198, 1391-1399)

In chronic allergic stimulation the mast cells and eosinophils releases nerve growth factor which causes growth of the nerves in the region. Thereby allowing for increased neural responses and hyper reactivity. This hyper reactivity is not limited to allergic reactions but extends to non-allergic conditions such as respiratory tract infections including viral and bacterial infections. Specifically viral rhinitis, viral and bacterial sinusitis, suppurative otitis media, bronchitis and pneumonia. Therefore individuals become more susceptible to these conditions and have more frequent and severe infections.

Furthermore the repeated allergic reactions cause changes in the qualitative response of the neural reflexes such that they are inappropriately activated. This negatively effects non-allergic conditions, such as bronchospasm mucus production and coughing in non-allergic lung conditions such as bronchitis and emphysema.

Allergic Reactions Differ from Inflammatory Reactions

Allergic reactions differ from inflammation. Allergies represent the body's inappropriate response to what is in essence a harmless antigen. It is believed that the IgE allergic reactions evolved to combat parasitic infections which are now rare in industrialized societies. In contrast, inflammation is the body's response to actual tissue damage or infection. Inflammation is clinically distinguished by the classical symptoms of calor, rubor and dolor: heat, redness and pain. Inflammation is a process that triggers a cascade of mediators with wide effects, both locally and systemically. Local reactions include pain, vasodilation and migration of macrophages and neutrophils. Systemic reactions include fever. Certain conditions, such as rhinitis or asthma, can be triggered by allergies, infections, irritating chemicals or may be entirely neurogenic, the result of nerve activity without prior inflammatory or allergic stimulation.

Specific Allergic Conditions

Rhinitis

Allergic Rhinitis

The inner lining of the nose is a mucosa that contains serous and mucus glands and large numbers of mast cells. This mucosa extends to the openings leading to the sinuses as well as the Eustachian tube where it is continuous with the mucosa of the sinuses and middle ear, respectively. The EPR of the nasal mucosa causes mast cell degranulation. The release of histamine, heparin and neuropeptides provokes vasodilation and acute swelling of the mucosa and has some minor direct stimulatory effect on the mucus secreting glands. Reflex excitation causes reflex sneezing, congestion and neural stimulation of the seromucinous glands and further congestion. LPR attracts eosinophils and prolongs the reaction.

Allergic reactions can also be chronic, a condition known as perennial rhinitis. In these cases airborne allergens are constantly in the environment. Chronic low-level allergic reactions cause a thickening of the nasal mucosa due to edema and hypertrophy of glandular elements. As a result the primary symptoms of perennial rhinitis are nasal congestion, and postnasal drip. After each allergic reaction the mucosa swells; repeated allergic reactions enlarges the mucosa permanently and may form polyps. Thickening of the mucosa can cause obstruction of the small openings that allow drainage from the sinus. Obstruction of these openings allows nasal secretions to collect and become infected, thereby causing sinusitis.

Topical treatment of allergic rhinitis includes steroid sprays and chromalyn sodium (Nasocrom®) a chemical that blocks mast cell degranulation, and/or nasal decongestants (Neosynephrine). Systemic treatment includes oral antihistamines and non-sedating antihistamines (Allegra®, Zyrtec®, Claritin®). Long-term therapy requires immune desensitization to the allergen by progressive intradermal injections of the allergen over months to years. rhinitis can lead Allergic rhinitis can lead to pulmonary disease, including but not limited to asthma and emphysema, suitably asthma caused by hyperreactivity and/or the symptoms of bronchoconstriction, mucosal edema, increased secretions and cough. These can be treated by the application of CnT to the nasal cavity of patients with allergic rhinitis. It is well known in the art that allergic conditions of the nose can cause reflex changes in the lung that mimic or exacerbate asthma. (McCusker C et al 2002, Site-specific sensitization in a murine model of allergic rhinitis: Role of the upper airway in lower airway disease, J Allergy Clin Immunol, 110:891-898)

Perennial Allergic Rhinitis

Perennial rhinitis is a chronic condition and certain symptoms, such as nasal congestion, are more prominent then others such as sneezing. Therefore therapy for this condition needs to be over more prolonged period, if not indefinitely. Although the same treatments as disclosed for seasonal allergic rhinitis can be used repeatedly, certain methods of treatment are disclosed here that are more efficient and convenient for longer term therapy.

Parasympathetic neurons do not extend from the central nervous system to their target organs in the nose. Instead parasympathetic preganglionic neurons have their cell bodies in the brain stem and have an axon that extends partway and synapses on the cell body of a second neuron called the postganglionic neuron. The axons of the postganglionic neurons extend into nose and sinuses and modulate many of the biological responses seen during allergic reactions. The cell body of the post ganglionic parasympathetic neuron also receives collateral afferent synapses from sensory neurons that are stimulated during allergic reactions. Therefore much of the neuronal circuit involved in the allergic reaction converges onto the cell body of the postganglionic neuron.

All of the postganglionic neuron cell bodies are concentrated in small structure called the sphenopalatine ganglion. Moreover all afferent synaptic connections on these neurons is cholinergic, the neurotransmitter most sensitive to BoNT. Therefore application of CnT to the sphenopalatine ganglion is the most efficient way of blocking the allergic neural reaction.

The sphenopalatine ganglion is accessible to needle injection via the sphenopalatine canal. This canal passes though the hard palate and is accessible about one centimeter medial to the second molar. Injections of anesthetic and vasoconstrictor agents are commonly performed by clinicians skilled in the art of nasal surgery.

Infectious Rhinitis

Although they share some of the same symptoms, allergic rhinitis differs from infectious rhinitis. The most common cause of infectious rhinitis is a viral infection, known as the common cold. Bacterial and fungal infections of the nose occur also but these are comparatively rare as primary events. During viral infections the epithelial cells release secretions that trigger an inflammatory response. The classic signs of caldor, rubor and dolor; heat, redness, and pain characterize inflammation. White blood cells such as macrophages and neutrophils migrate from small blood vessels in the area to the infected mucosa. These cells in turn release a variety of chemical mediators that increase the inflammation. Infectious rhinitis is characterized by a purulent or pus like postnasal drip, and nasal congestion. In many viral infections there are systemic symptoms such as fever. Treatment of viral infections is symptomatic with topical and systemic decongestants, and antipyretic and anti-inflammatory drugs.

Vasomotor and Other Causes of Rhinitis

Vasomotor rhinitis is strictly a neural hyper stimulation of the serous secretory glands of the nose. This condition is characterized by a watery nasal discharge with a very small content of mucus. Vasomotor rhinitis results directly from neural stimulation of temperature changes or while eating, and associated other symptoms such as congestion, and sneezing are not prominent. U.S. Pat. No. 5,766,605 discloses a method of blocking the symptom of rhinorrhea in vasomotor rhinitis using *clostridia* neurotoxins.

Serous Otitis Media

Direct reaction of the middle ear mucosa to allergens, or indirect effects by blockage of the Eustachian tube, leads to serous otitis media. In this condition the middle ear fills with fluid and hearing is impaired. As this condition most often affects young children, they are at risk of learning disabilities due to the decreased hearing acuity.

Sinusitis, a Complication of Rhinitis

Sinusitis is an infection of the sinuses. The sinuses are air filled cavities surrounding and opening into the nasal cavity via small openings called ostia. The maxillary sinuses compose the mass of the cheeks and the ostia are between the inferior and middle turbinate. The frontal sinuses are above the brow underneath the skin of the forehead, they open into the nasal cavity via a duct that enters beneath the middle turbinate. The sphenoid sinuses are in the nasopharynx and have ostia on their anterior surface. The ethmoid sinuses are located between the eyes and are composed of numerous small air cells. The anterior and posterior cells drain independently. The anterior ethmoid region is especially important due to the confluence of drainage ostia. The area is called the infundibulum, and a small amount of obstruction can cause widespread sinus infections.

Sinus infections are either acute or chronic. In acute sinusitis a bacterial infection follows a viral infection of the upper respiratory tract. However, sinusitis can also occur from obstruction of the draining ostia of the sinuses by inflammation or mass lesion. Topical nasal decongestants and systemic antibiotics are used to treat acute sinusitis. Severe or complicated infections may require surgical drainage of the involved sinus. Chronic sinusitis is a low-grade ongoing or recurrent infection of the sinuses. In these cases the mucosa of the sinuses has become thickened and enlarged due to edema and increased secretory glandular elements. In these cases small abscess may persist and relatively mild inflammatory stimuli may cause obstruction of the narrowed sinus ostia. Treatment of chronic sinusitis includes topical steroid sprays, systemic anti histamines and decongestants, and/or surgical removal of diseased mucosa with enlargement of the ostia.

Asthma

Asthma is a general term given to a similar constellation of symptoms: bronchospasm, mucosal swelling and increased secretions. Allergic stimulation, infections, irritating chemicals, cold air or exercise can trigger asthma.

Allergic asthma is a specific subset of asthma that is initiated by allergens and involves the IgE mediated reaction. Local and organ reactions include bronchial smooth muscle constriction, mucosal swelling and increased secretions.

Other Allergic Conditions

Other allergic conditions include food allergies, and allergic dermatitis.

Clostridia Neurotoxins (CnT)

*Clostridium* (C.) *botulinum* and the closely related species *C. butyricum* and *beratti* produce an extremely powerful neurotoxin that causes the paralytic condition known as botulism. The *botulinum* neurotoxin (BoNT) protein consists of a light and heavy chain that together weigh approximately 150 kD. In botulism the primary target is the synapse of the motor neuron with the muscle fiber. Here BoNT is taken up by the membrane of the motor neuron and is internalized. The effect of BoNT is to inhibit the release of neurotransmitters and neuropeptides by neurons. In clinical use each serotype appears to differ in its potency in blocking different classes of neurons.

BoNT works by a two-stage mechanism, uptake and molecular action. Peripheral nerve terminals take up BoNT. After translocation across the cell membrane BoNT interferes with the molecular mechanism of neurosecretion. Specifically, BoNT cleaves the proteins involved in synaptic vesicle docking and release called the SNARE complex. The result is to block neural signals.

*C. tetani* produce tetanus neurotoxin (TeNT). TeNT is similar to the BoNTs in that it interferes with vesicle release by cleaving VAMP, one of the SNARE family of proteins. However the in vivo biological activity of TeNT is usually quite different from BoNT. The systemic disorder tetanus results from TnT produced at a wound site and disseminated throughout the body via the blood stream. The TeNT is taken up by peripheral motor neurons and transported to the central nervous system. The TeNT then preferentially blocks inhibitory neurons connecting to the motor neuron, thereby allowing unopposed excitatory input. However, at higher doses TeNT and when introduced directly into the neuron also blocks all neurons in the same manner as BoNT. In this application it is assumed that the when BoNT is discussed, it includes the TeNT when used at higher blocking doses.

At present seven immunologically distinct serotypes of the BoNT are known, named A, B, C, D, E, F and G. The type C serotype is now known to be divided into three different toxins with distinct biological effects. Only C1 is a neurotoxin, whereas C2 and C3 are not. C2 is distinctive for blocking actin formation, which can prevent mast cell degranulation. Although all BoNT serotypes interfere with proteins that cause the release of synaptic vesicles from cells they each interfere with different proteins, or different parts of the same protein:

BoNT A & E cleave SNAP-25 (synapse associated protein)

BoNT C cleaves SNAP-25 and syntaxin

BoNT B, D, F & G (and TeNT) cleave VAMP (vesicle associated membrane protein)

Most if not all cell types use the vesicle system for secretion, although the molecules within these vesicles differ for each type of cell. If experimentally introduced into any cell BoNT appears capable of blocking its vesicle release. However, in nature BoNT appears to be internalized into neurons, particularly the efferent neurons. The vesicles within neurons contain classical neurotransmitters (acetylcholine, epinephrine, nor epinephrine, dopamine, serotonin, glutamate, GABA and others) and/or neuropeptides (substance P, neurokinin A, calcitonin gene related peptide (CGRP), neuropeptide Y, interleukins, growth factors and others). Although the highest affinity of BoNT is for cholinergic neurons, in various preparations BoNT has been shown to block secretion of all these molecules.

The Clinical Effects of *Botulinum* Toxin on Different Classes of Neurons Voluntary Motor Nerves The first and still primary use of BoNT is to block motor nerve communication with muscle fibers. BoNT is injected within the target muscle. The BoNT is then internalized into motor neurons where it decreases or stops the release of the neurotransmitter acetylcholine (AChE), thereby causing paresis or paralysis of the muscle. Scott introduced the concept of localized muscular injections of BoNT in the specific condition of strabismus (squint, crossed eyes). Later BoNT was found to be particularly useful for movement disorders such as tics, spasms, contractures, cramps and tremors. More recently, the injection of BoNT into facial muscles has been found to ameliorate skin wrinkling and lines related to aging. Another recent application of BoNT injections is to decrease the pain accompanying muscle tension in conditions such as headache and temporo-mandibular joint syndrome.

Autonomic Motor Neurons

Effector neurons of the autonomic system innervate and control the contraction of smooth muscles using AChE as the neurotransmitter. Injections of BoNT have been used to decrease tone in the smooth muscles of the lower esophageal sphincter, esophagus, stomach wall, and pyloric sphincter, sphincter of Odi, anal sphincter, and urinary bladder.

Autonomic Secretory Neurons

Effector neurons of the autonomic system control or modulate the secretion of various water and mucoid fluids throughout the body. BoNT injections have been used to decrease sweating, salivary gland flow, gastric secretions including acid production, nasal and other respiratory secretions, and tearing.

Sensory Neurons

Sensory neurons release a wide variety of neuropeptides, cytokines, growth factors and other substances that effect parenchymal cells, blood vessels and immune cells. Notable is that these substances can activate mast cells directly thereby extending the allergic reaction. Except for nitrous oxide these substances are released via the SNARE mechanism and can be blocked by CnT.

SUMMARY OF THE INVENTION

As used herein 'local administration' includes but is not limited to injection by needle and in-dwelling catheter (including pressure jet injectors), topical administration in lyophilized powder, liquid solutions, creams, ointments, aerosolized or introduced by liposomal (niosomes) vectors, or as nucleic acid introduced by viral or other vectors. The CnT may also be embedded in biopolymers or delivered by implanted pumps to release the CnT into solution over prolonged periods.

By "therapeutically effective amount" it is meant of purposes of this invention that the CnT is administered in a non-toxic amount sufficient to cause reduction in the occurrence or magnitude of the symptoms being targeted.

By "unit" it is meant the biological equivalent of the current unit measure used for *botulinum* toxin A marketed as Botox. At present BoNT is measured by biological assay; a unit of BoNT is the amount that causes death to 50% of mice when injected intraperitoneally. BoNT-A is marketed as Botox by Allergan Corp, Irvine Calif., and as Dysport by Ipsen Ltd, Berks United Kingdom. Although the biological assay is done the same way the in vivo effect of Botox and Dysport vary. BoNT-B is marketed as Myobloc by Elan Pharmaceuticals, Dublin, Ireland. TeNT is not commercially available but other assays have compared the potency of the blocking effect of TeNT to BoNT. All serotypes of BoNT as well as TeNT are commercially available from List Biological Laboratories. A therapeutically effective amount of BoNT will vary depending on the organ to be treated, how much of the organ will be treated, the method of application and the exact preparation of BoNT used. A therapeutically effective amount will vary from a fraction of a unit to hundreds of units as is it currently does with intramuscular injections. The exact dosage will not require undo experimentation by those skilled in the art.

Where solutions or suspensions of BoNT or CnT are referred to, unless indicated to the contrary, this means the designated number of units in 1 ml of Normal saline.

By "CnT" it is meant that any biological substance having essentially the same biological effect within cells as the wild types of *clostridia* neurotoxins. Specifically, to block or decrease the activity of the SNARE family of proteins involved in secretion of allergy related neurohumors. Numerous substitutions for the major parts of the CnT have been disclosed and these are all included in this specification. This would include fragments, altered forms, and recombinant forms of CnT. Also included are chimeras, hybrids and conjugates. Also included are the use of DNA and RNA sequences that are directly applied and translated in the allergic sites. Also included are "vectors", various compositions that deliver a *botulinum* or tetanus toxin light chain or its equivalent such as Protease A across cell membranes. These vectors include but are not limited to viruses, liposomes, noisomes, and protein transduction domains (U.S. Provisional Application 60/449,107).

Allergic "neurohumors" are neurotransmitters, neuropeptides and cytokines that participate in allergic reactions and whose secretion or action can be blocked by CnT. They include acetylcholine, noradrenaline, neuropeptide Y, substance P, calcitonin gene reactive protein (CGRP), histamine, nerve growth factor, and interleukins.

The invention is directed to a method of blocking or reducing physiological reaction in a mammal, suitably but not limited to *H. sapiens*, to the interaction of IgE antibodies present in said mammal upon contact with the corresponding antigen. This blocking is achieved by the administration to said mammal of a therapeutically effective amount of a neurotoxin (CnT) derived from *Clostridia* sp. Suitably, the CnT is derived from a species of *Clostridia* selected from the group consisting of *C. botulinum, C. butyricum, C. beratti, C. tetani*. The neurotoxins (BoNT), derived from *C. botulinum*, are derived from serotypes A, B, C1, D, E, F and G, while neurotoxin (TeNT), is derived from *C. tetani*

BoNT/A is marketed as Botox®. by Allergan Inc and as Dysport®. by Ipsen Ltd as a lyophilized powder that is reconstituted with preservative free normal saline prior to use. BoNT/B is marketed as Myobloc®. by Elan Pharmaceuticals in normal saline solution. The light chains and holotoxins for each BoNT serotypes and TeNT can be obtained from List Biological Labs and/or Metabologics Inc.

CnT compositions of the present inventions are prepared in a variety of forms depending on whether the composition is injected or implanted, topically applied to respiratory mucosa of the nasal cavity or lungs, gastrointestinal mucosa, or to skin.

For all injectable CnT compositions fluid dosage forms are prepared utilizing the compound and a pyrogen-free sterile vehicle. The compound, depending on the vehicle and concentration used, can be either dissolved or suspended in the vehicle. In preparing solutions the compound can be dissolved in the vehicle, the solution being made isotonic if necessary by addition of sodium chloride and sterilized by filtration through a sterile filter using aseptic techniques before filling into suitable sterile vials or ampoules and sealing. Alternatively, if solution stability is adequate, the solution in its sealed containers may be sterilized by autoclaving. Advantageously additives such as buffering, solubilizing, stabilizing, preservative or bactericidal, suspending or emulsifying agents and/or local anaesthetic agents may be dissolved in the vehicle.

Dry powders, which are dissolved or suspended in a suitable vehicle prior to use, may be prepared by filling pre-sterilized drug substance and other ingredients into a sterile container using aseptic technique in a sterile area. Alternatively the drug and other ingredients may be dissolved into suitable containers using aseptic technique in a sterile area. The product is then freeze-dried and the containers are sealed aseptically.

In the respiratory and gastrointestinal systems, CnT binds to mucosal epithelial cells and is actively transcytosed across the mucosa. Compositions suitable for administration to the respiratory tract include aerosols, nebulisable solutions or micro-fine powders for insufflation. In the latter case, particle size of less than 50 microns, especially less than 10 microns, is preferred.

Compositions suitable for topical mucosal application include normal saline solutions as described above for injections. Other suitable compositions include gels and creams.

The skin presents a formidable barrier to the application of CnT. CnT may be mechanically propelled across the dermal barrier with air or water pressure injectors or in association with micropellets. Other suitable forms of transdermal delivery include iontophoresis. CnT may be encapsulated into liposomes or niosomes to form suitable transdermal compositions.

The method of administration may take many forms, including topical, intra-dermal, subcutaneous, trans-cutaneous, intra cavital and by inhalation of the CnT in a suitable carrier. Examples of such administration include, but are not limited to contact with absorbant pledgets having CnT absorbed thereon, contact with biodegradable micropellets having CnT embedded therein. Also included is injection, for example, injection to the nasal mucosa or injection into the pterygoplatine space through the palate, or injection into affected areas of the surface skin, more invasively, by myringotomy and injection into the middle ear space or tympanic membranes. Alternatively less invasive methods include by drops into the inner eyelid and inhalation of an aqueous mist containing same.

The physiological reaction reactions dealt with herein include but are not limited to conditions such as allergic rhinitis, infectious rhinitis, vasomotor rhinitis, serous otitis media, sinusitis, asthma, food allergies and allergic dermatitis.

The amount of CnT administered per administration may be, but is not limited to between about 0.1 and about 1000 units, suitably between about 1 and about 100 units per administration, preferably between about 1 and about 20 units.

The invention is also directed to use of a neurotoxin (CnT) derived from *Clostridia* sp. for the production of a medicament for blocking or reducing physiological reaction in a mammal to the interaction of IgE antibodies present in said mammal upon contact with the corresponding antigen. The formulations of CnT, including BoNT and TeNT, which are suitable for the purposes designated herein are well known, but have not previously been designated for this purpose.

There is a great need for an effective treatment for allergic disorders. It has long been thought that the allergic reaction involved only histamine release by mast cells. Therefore first line therapy for allergy was antihistamines, or more recently the non-sedating antihistamines. Other therapies are directed to block the effects of the mast cell secretions with adrenergic agonists. It is not obvious to those skilled in the art that a central role in allergic disorders involves the autonomic nervous system and that this nerve activity can be blocked by CnT for a beneficial effect.

It is an object of the invention to provide a treatment for allergic conditions. Included particularly are allergy related rhinitis, asthma, gastroenteritis, serous otitis, sinusitis and dermatitis and their related conditions (such as sinusitis and serous otitis media that occur secondary to allergy induced mucosal swelling). Treatment is by local application of therapeutically effective amounts of CnTs to the body structure and/or the nerves and nerve ganglia supplying these structures. CnT interfere with the allergic process by:
1) Directly blocking neuroimmune secretions by the mast cell or other immune cell types including but not limited to eosinophils
2) Block the release of neurohumors by mast cells induced by autonomic nerve activity.
3) Decrease neurohumoral release during axonal reflexes.
4) Decrease the parasympathetic effector arm of reflex allergic responses
5) Decrease the increased tonic activity of the autonomic systemic that is related to prior allergic reactions.
6) Decrease the enlargement and hypersensitivity of sensory nerves induced by nerve growth factor and other neurohumors released during allergic reactions.
7) Reverse certain complications of allergic reactions such as mucosal thickening by decreasing autonomic nerve activity.

The beneficial effect of this treatment in the:
1) Nasal area, is to decrease the symptoms of sneezing, itching, nasal congestion and post nasal drip, as well as related conditions including nasal polyps and mucosal thickening, and complications such as sinusitis and serous otitis.
2) Lungs, is to decrease coughing and wheezing (bronchoconstriction, edema) and the non-specific sensory hypersensitivity related to chronic allergic reactions.
3) Eye, is to decrease itching, tearing and redness.
4) Skin, is to decrease itching and swelling.
5) Gastrointestinal tract, is to decrease gastrointestinal dysmotility.

EXAMPLES

Example 1. Seasonal Allergic Rhinitis

1a) A 30-year-old male has seasonal allergic rhinitis. In May, prior to pollen formation, 30 units of BoNT were topically applied in each nostril. Specifically, the nasal cavity is sprayed with a solution of 1% lidocaine and ½% neosynephrine to anesthetize and decongest the nasal mucosa, respectively. Then 1 cc of normal saline containing 30 units of BoNT is sprayed into each nasal cavity. This method of delivery, although commonly used for application of nasal medication, is inherently inefficient as a significant percentage of a sprayed medication will exit the posterior nasal cavity and be exhaled or swallowed.

1b) In another embodiment, the patient is treated by placing 1×3 $cm^2$ cotton pledgets impregnated with 20 units of BoNT onto the medial surface of the turbinates and left for one hour, then removed by the physician. This delivery method is more efficient then a spray, however a significant percentage of the BoNT will not diffuse from the pledgets to the mucosa.

1c) Alternatively, the patient has topical anesthesia applied only to a localized area, preferably the anterior end of the inferior turbinate. Then, patient has a 1 $cm^2$ cotton pledget impregnated with 10 units of BoNT placed onto the mucosa of the anterior turbinate for one hour and then removed. Within the nasal cavity a mucociliary blanket transports fluids and particles posteriorly, thereby distributing the BoNT. This is an example of applying a BoNT to a localized region of the nasal cavity and using the normal physiology of the nasal cavity for distribution. The routes of mucociliary clearance of the nose and sinus cavities are known so that other variations of this method are apparent to those skilled in the art.

1d) In another embodiment, using a topical biodegradable depot to deliver BoNT over an extended time period to nasal mucosa is used for treating the patient. Various biodegradable compounds are known in the art that vary in consistency and rate of dissolution.

An example is oxidized cellulose (marketed as Surgicel®. by Johnson & Johnson, New Brunswick, N.J.). The oxidized cellulose can be manufactured with BoNT as an integral component, or the BoNT can be added to the oxidized cellulose before its clinical use. Surgicel is available in the form of a thin flexible sheet that is often cut to fit the area of the body to which it will be applied. For intranasal use the size may vary from a few square millimeters to a 4 by 8 $cm^2$ sheet that could contact the entire exposed mucosa of the nasal cavity. BoNT can be added to the Surgicel as a lyophilized powder or after reconstitution into solution. If added as a powder it can homogeneously applied onto one side of the Surgicel and the material can be folded. The material is then moistened with normal saline to bind the material together and immobilize the BoNT prior to clinical use. In contrast the BoNT can first be constituted into solution and then absorbed into the material.

As an example a 2×6 $cm^2$ piece of oxidized cellulose is saturated with 1 cc of normal saline containing a total of 10 units of BoNT. Using a nasal speculum the nostril is dilated and the nasal cavity is visualized and the saturated cellulose place therein. The cellulose will gradually dissolve over hours while releasing a small continual dose of BoNT directly onto the nasal mucosa.

Alternatively the patient is administered 0.5 cc. of normal saline containing 5 units of BoNT is applied to the oxidized cellulose which is grasped with bayonet forceps and placed flat onto the medial surface of the anterior end of the inferior turbinate of each nasal cavity. As disclosed above the mucociliary action of the nasal mucosa transports liquids and particles from the anterior to posterior nasal cavity.

1e) In another embodiment the patient is injected with BoNT solution directly into the nasal mucosa. After anesthetizing and decongesting the mucosa, 5 units of BoNT in 1 cc of saline are injected beneath the mucosa throughout the length of the inferior turbinate with a 25 gauge spinal needle coupled to a 1 cc syringe.

1f) Alternatively the patient can be treated with TeNT.

Compositions of TeNT for intranasal administration, can range in dose from 0.1 to 1000 units in 0.1 cc to 10 cc of solution. One preferable composition is 10 units of TeNT in 1 cc of normal saline.

As an example the same patient is treated by spraying each nostril with 1 cc of normal saline solution containing 10 units of TeNT.

Alternatively, if only decongestion is desired 10 units of TeNT can be topically applied.

In another embodiment, 1 unit of recombinant DNA coding for TeNT is pressure injected across the nasal mucosa to transfect mucosal cells. These cells then express the TeNT for months.

Example 2. Perennial Allergic Rhinitis

2a) Direct injection of the sphenopalatine ganglia.

A 40-year-old female has chronic nasal congestion due to perennial rhinitis. Skin testing demonstrates that she is allergic to numerous environmental antigens and intranasal examination shows enlarged turbinate mucosa and nasal polyps. Testing of nasal secretions shows eosinophilia. An injection of 20 units of BoNT in a 1 cc solution of normal saline is made through the sphenopalatine canal into the area of the sphenopalatine ganglia.

In another embodiment, 100 units of BoNT embedded in 0.1 micron biodegradable pellets suspended in solution is injected into the mucosa of each turbinate to slowly release its contents over 6 months.

Alternatively a biodegradable carrier containing 5 units of BoNT is placed intranasally in the most superior and posterior aspect of the lateral nasal wall. This permits the BoNT to diffuse across the nasal wall to the underlying sphenopalatine ganglia.

Example 3. Serous Otitis Media

A 3-year old male has a history of serous otitis media. Under general anesthesia a myringotomy is made into the tympanic membranes and 2 units of BoNT in 0.5 cc of normal saline is injected.

Example 4. Sinusitis

A fifty-year-old male has a history of allergic rhinitis and recurrent sinusitis. Ten units of BoNT are injected through the palate into the pterygopalatine space to block the sphenopalatine ganglion.

Example 5. Allergic Dermatitis

A seventy-year-old male has severe allergic dermatitis of the forearm skin. Each forearm is injected with 10 injections of 0.3 units BoNT in 0.1 cc of normal saline. Each injection is made intradermally at 3 cm intervals.

Example 6. Allergic Asthma

A 13-year-old boy has severe allergic asthma. He is treated by bimonthly inhalation therapy of an aerosilized solution of 5 units of *botulinum* toxin in 5 cc of normal saline.

Alternatively the same *botulinum* solution can be injected directly into the trachea and bronchi. After injecting local anesthesia into the skin overlying the cricothyroid membrane a needle is passed directly through the skin and cricothyroid membrane and the BoNT solution is sprayed into the trachea. The solution drips down to reach the bronchial mucosa where it is topically absorbed.

Example 7. Allergic Rhinitis

A 40-year old male has allergic rhinitis and an associated reflex chronic cough. Application of CnT to the nasal cavity as described above or alternatively injected or aerosilized topical application of BoNT to the lungs is used to treat the cough.

Example 8. Food Allergies

A 10-year-old boy with food allergies manifested by bloating and diarrhea is treated with a rectal suppository containing 50 units of BoNT. The suppository is composed of biocompatible material designed to be solid at room temperature but to dissolve at body temperature. Sufficient materials for the composition are cocoa butter, glycerinated gelatin, hydrogenated vegetable oils, polyethylene glycols of various molecular weights and fatty esters of polyethylene glycol.

Example 9. Infectious Rhinitis

Chronic allergic exposure causes the nervous system to become hyper responsive to non-allergic stimulation such as that caused by viral infections.

A patient with rhinitis is given 10 units of BoNT and 5 units of TeNT prior to spring.

I claim:

1. A method of blocking or reducing the symptoms of allergic rhinitis in a mammal including sneezing, itching or nasal congestion, the method comprising administering to the mammal a therapeutically effective amount of a *botulinum* neurotoxin, wherein the *botulinum* neurotoxin is administered directly to a postganglionic parasympathetic neuron of the mammal to block and reduce the symptoms of the allergic rhinitis.

2. The method of claim 1, wherein the postganglionic parasympathetic neuron is a sphenopalatine ganglion.

3. The method of claim 1, wherein the *botulinum* neurotoxin is administered by injection.

4. The method of claim 1, wherein the *botulinum* neurotoxin is administered topically.

5. The method of claim 1, wherein the *botulinum* neurotoxin is administered by inhalation.

6. The method of claim 1, wherein the *botulinum* neurotoxin is administered using a topical biodegradable depot comprising the *botulinum* toxin.

7. The method of claim 1, wherein the *botulinum* neurotoxin is selected from the group consisting of *botulinum* neurotoxin serotypes A, B, C1, D, E, F or G.

8. The method of claim 1, wherein the *botulinum* neurotoxin is *botulinum* neurotoxin serotype A.

9. The method of claim 8, wherein the therapeutically effective amount is at least 10 units of *botulinum* neurotoxin serotype A.

10. The method of claim 8, wherein the therapeutically effective amount is at least 20 units of *botulinum* neurotoxin serotype A.

11. A method of blocking or reducing allergic rhinitis in a mammal, the method comprising administering to a sphenopalatine ganglia of the mammal at least 10 units of a *botulinum* neurotoxin serotype A to treat the allergic rhinitis.

12. The method of claim 11, wherein the *botulinum* neurotoxin is administered by injection.

13. The method of claim 11, wherein the *botulinum* neurotoxin is administered topically.

14. The method of claim 11, wherein the *botulinum* neurotoxin is administered by inhalation.

15. The method of claim 11, wherein the *botulinum* neurotoxin is delivered to the nasal mucosa of the mammal.

16. The method of claim 11, wherein the *botulinum* neurotoxin is administered by injection into the pterygopalatine space through the palate.

17. The method of claim 11, wherein the *botulinum* neurotoxin is administered to pass through the sphenopalatine canal into the area of the sphenopalatine ganglia.

\* \* \* \* \*